(12) United States Patent
Stetzer

(10) Patent No.: US 11,202,864 B2
(45) Date of Patent: Dec. 21, 2021

(54) SYRINGE HOLDER FOR USE IN ANESTHESIOLOGY

(71) Applicant: Joan Stetzer, Pewaukee, WI (US)

(72) Inventor: Joan Stetzer, Pewaukee, WI (US)

( * ) Notice: Subject to any disclaimer, the term of this patent is extended or adjusted under 35 U.S.C. 154(b) by 273 days.

(21) Appl. No.: 16/573,739

(22) Filed: Sep. 17, 2019

(65) Prior Publication Data

US 2021/0077733 A1 Mar. 18, 2021

(51) Int. Cl.
*A61M 5/31* (2006.01)
*A61M 5/315* (2006.01)

(52) U.S. Cl.
CPC ...... *A61M 5/3137* (2013.01); *A61M 5/31513* (2013.01); *A61M 5/31551* (2013.01); *A61M 2202/048* (2013.01); *A61M 2209/084* (2013.01)

(58) Field of Classification Search
CPC ........ A61M 5/3137; A61M 2005/3139; A61M 5/31513; A61M 5/31551; A61M 2202/048; A61M 2209/084; A61M 5/315; A61M 5/31533; A61M 5/31555; A61M 5/3159; A61M 5/31593; A61M 5/31595
See application file for complete search history.

(56) References Cited

U.S. PATENT DOCUMENTS 2,952,255 A * 9/1960 Hein, Jr. ........... A61M 5/31555
604/210
3,610,241 A * 10/1971 LeMarie ............. A61M 5/1782
604/407

* cited by examiner

*Primary Examiner* — Brandy S Lee
*Assistant Examiner* — Hong-Van N Trinh
(74) *Attorney, Agent, or Firm* — Reinhart Boerner Van Deuren s.c.

(57) ABSTRACT

A syringe holder includes a syringe barrel holder having a depression which is configured to receive and engage finger tabs of a syringe and has a bottom depression surface engageable by the finger tabs. A barrel opening receives a barrel of the syringe, and includes a central longitudinal axis, a shaft channel and a set screw channel having a screw axis passing through the shaft channel. A dosing shaft extends from a first end to a second end and includes a plurality of notches between the ends. The dosing shaft is located and slideable within the shaft channel. A plunger cap includes a plunger receptacle and attaches to a first end of the dosing shaft. A socket set screw is located and engaged within the set screw channel and has a resilient end engageable with the notches of the dosing shaft.

20 Claims, 8 Drawing Sheets

SYRINGE HOLDER FOR USE IN ANESTHESIOLOGY

BACKGROUND OF THE INVENTION

The present disclosure relates generally to the field of delivery of anesthetic drugs. The present disclosure relates specifically to a syringe holder for delivering an anesthetic drug. The syringe holder is hand-held and is operated by a user to directly deliver a regular, discrete amount of an anesthetic drug to a patient during a surgical procedure.

SUMMARY OF THE INVENTION

A syringe holder, for holding a syringe including a barrel and a plunger, the barrel defined by a length and an end pair of finger tabs, with a hole there-between, opposite an open end to dispense an anesthetic drug, the plunger defined by a length and a finger pad opposite a rubber seal, includes a syringe barrel holder extending between a top surface and a bottom surface and bounded by an exterior surface extending there-between. The syringe barrel holder has a depression in the top surface which is configured to receive and engage the finger tabs of the syringe and has a bottom depression surface which is engageable by the finger tabs. A barrel opening receives the barrel of the syringe, and includes a central longitudinal axis, a shaft channel having a shaft axis parallel to the central longitudinal axis, and a set screw channel having a screw axis passing through the shaft channel. A dosing shaft extends from a first end to a second end and includes a plurality of notches between the ends. The notches are equally spaced. The dosing shaft is located and slideable within the shaft channel. A plunger cap includes a plunger receptacle and is attached to the first end of the dosing shaft such that the plunger receptacle receives the finger pad of the plunger when the syringe is positioned in the barrel opening. A socket set screw is located and engaged within the set screw channel and has a resilient end engageable with the notches of the dosing shaft to permit discrete positioning of the dosing shaft within the shaft channel.

A syringe holder, for holding a syringe including a barrel and a plunger, the barrel defined by a length and an end pair of finger tabs, with a hole there-between, opposite an open end to dispense an anesthetic drug, the plunger defined by a length and a finger pad opposite a rubber seal, includes a syringe barrel holder extending between a top surface and a bottom surface and bounded by an exterior surface extending there-between. The syringe barrel holder has a depression in the top surface which is configured to receive and engage the finger tabs of the syringe and has a bottom depression surface which is engageable by the finger tabs. A barrel opening receives the barrel of the syringe, and includes a central longitudinal axis, a shaft channel having a shaft axis parallel to the central longitudinal axis, and a set screw channel having a screw axis passing through the shaft channel. The screw axis is perpendicular to and intersects with the shaft axis. A dosing shaft extends from a first end to a second end and includes a plurality of notches between the ends. The notches are equally spaced at increments of 3.0 mm to 4.0 mm. The dosing shaft is located and slideable within the shaft channel. A plunger cap includes a plunger receptacle and is attached to the first end of the dosing shaft such that the plunger receptacle receives the finger pad of the plunger when the syringe is positioned in the barrel opening. The plunger cap has an internal wall with a thickness from 3.40 mm to 4.40 mm. A socket set screw is located and engaged within the set screw channel and has a resilient end engageable with the notches of the dosing shaft to permit discrete positioning of the dosing shaft within the shaft channel.

A syringe holder, for holding a syringe including a barrel and a plunger, the barrel defined by a length and an end pair of finger tabs, with a hole there-between, opposite an open end to dispense an anesthetic drug, the plunger defined by a length and a finger pad opposite a rubber seal, includes a syringe barrel holder extending between a top surface and a bottom surface and bounded by an exterior surface extending there-between. The syringe barrel holder has a depression in the top surface which is configured to receive and engage the finger tabs of the syringe and has a bottom depression surface which is engageable by the finger tabs, and a first flange depression opposite a second flange depression to allow the finger tabs of the barrel to twist and lock into the depression. A barrel opening receives the barrel of the syringe, and includes a central longitudinal axis, a shaft channel having a shaft axis parallel to the central longitudinal axis, and a set screw channel having a screw axis passing through the shaft channel. The screw axis is perpendicular to and intersects with the shaft axis. A dosing shaft extends from a first end to a second end and includes a plurality of notches between the ends. The notches are equally spaced at increments of 3.0 mm to 4.0 mm. The dosing shaft is located and slideable within the shaft channel. A plunger cap includes a plunger receptacle and is attached to the first end of the dosing shaft such that the plunger receptacle receives the finger pad of the plunger when the syringe is positioned in the barrel opening. The plunger cap has an internal wall with a thickness from 3.40 mm to 4.40 mm. A socket set screw is located and engaged within the set screw channel and has a resilient end engageable with the notches of the dosing shaft to permit discrete positioning of the dosing shaft within the shaft channel.

Additional features and advantages will be set forth in the detailed description which follows, and in part will be readily apparent to those skilled in the art from the description or recognized by practicing the embodiments as described in the written description and claims hereof, as well as the appended drawings. It is to be understood that both the foregoing general description and the following detailed description are exemplary.

The accompanying drawings are included to provide a further understanding and are incorporated in and constitute a part of this specification. The drawings illustrate one or more embodiments and together with the description serve to explain principles and operation of the various embodiments.

DETAILED DESCRIPTION

Figure 1:
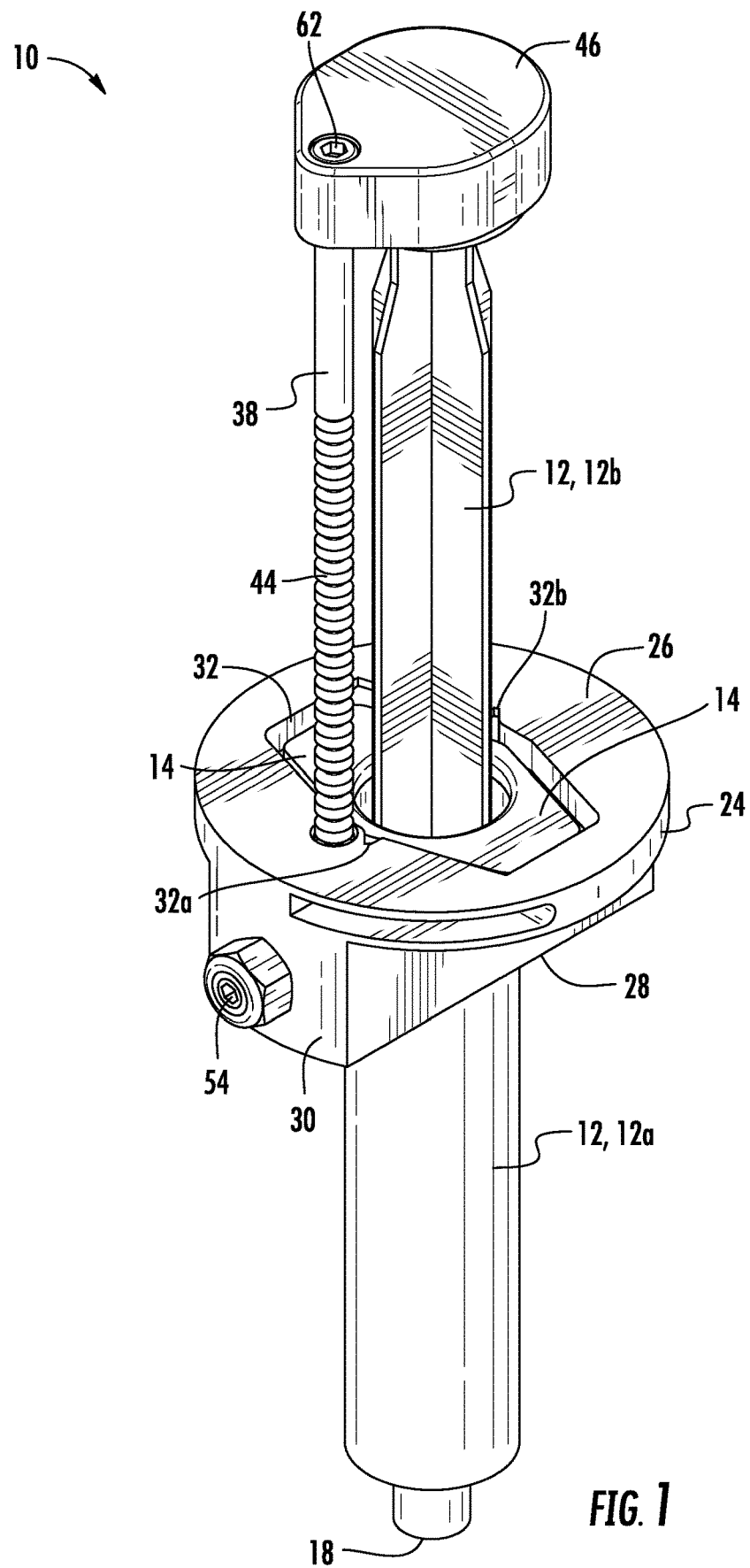
FIG. 1 is a perspective view of a syringe holder, according to an exemplary embodiment.
Figure 2:
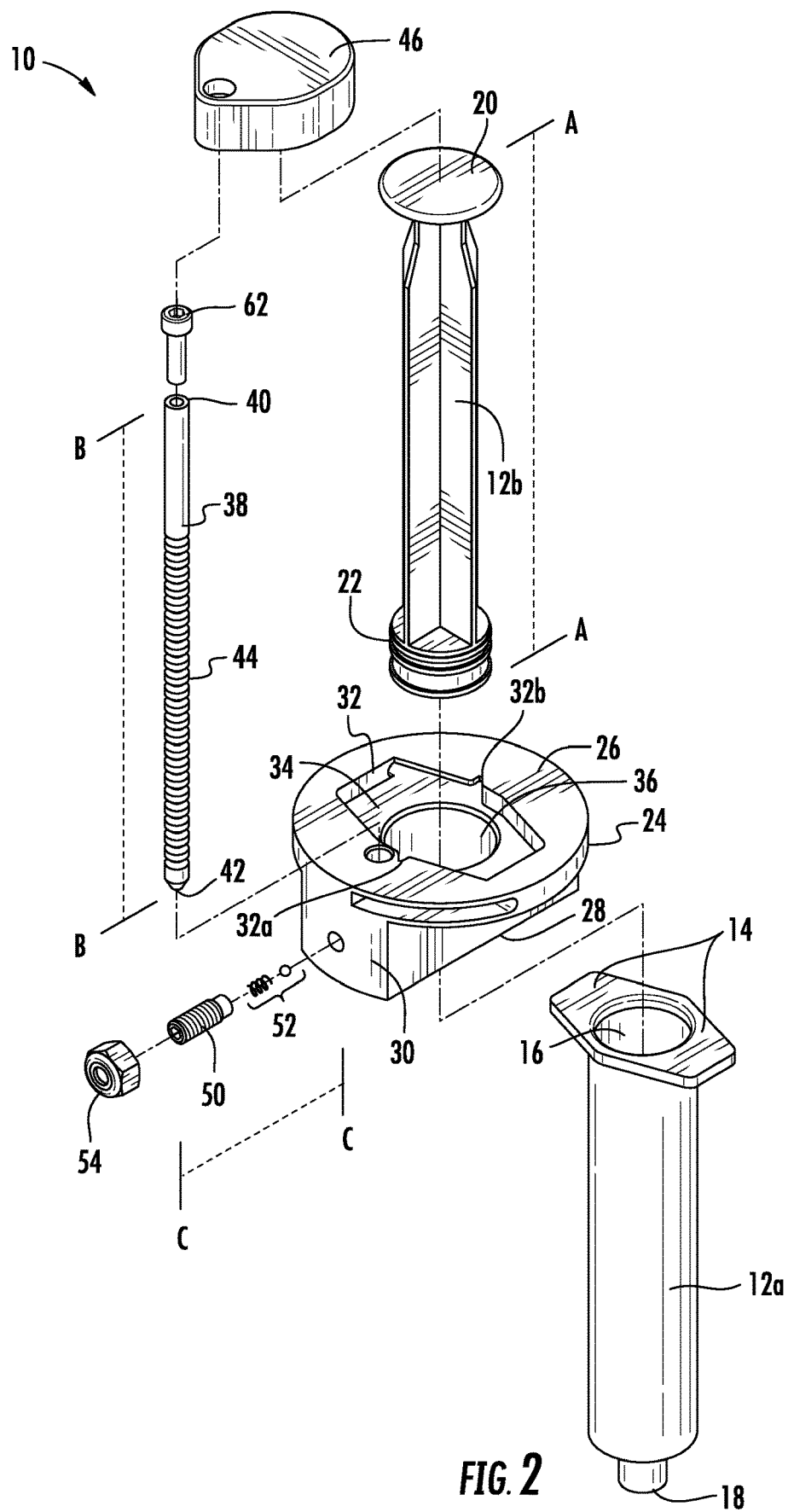
FIG. 2 is an exploded perspective view of the syringe holder of FIG. 1, according to an exemplary embodiment.

First illustrated in FIGS. 1 and 2 is a syringe holder 10, for holding a syringe 12. Syringe 12 includes a plastic barrel 12a and a plunger 12b. Barrel 12a extends between an open end having a pair of finger tabs 14, with an opening/hole 16 there-between, and a dispensing opening 18 at which a drug, such as an anesthetic drug, is dispensed. Plunger 12b includes a plastic, X-shaped (cross-section) shaft having a finger pad 20 at one end and a rubber seal 22 at the opposite end. Rubber seal 22 forms a sliding sealing engagement with an inside surface of barrel 12a to move fluid through dispensing opening 18 in response to relative movement between plunger 12b and barrel 12a. By way of example, syringe 12 may be a 20 cc syringe of the type sold by McKesson Corporation or Becton, Dickinson and Company.

Figure 10:
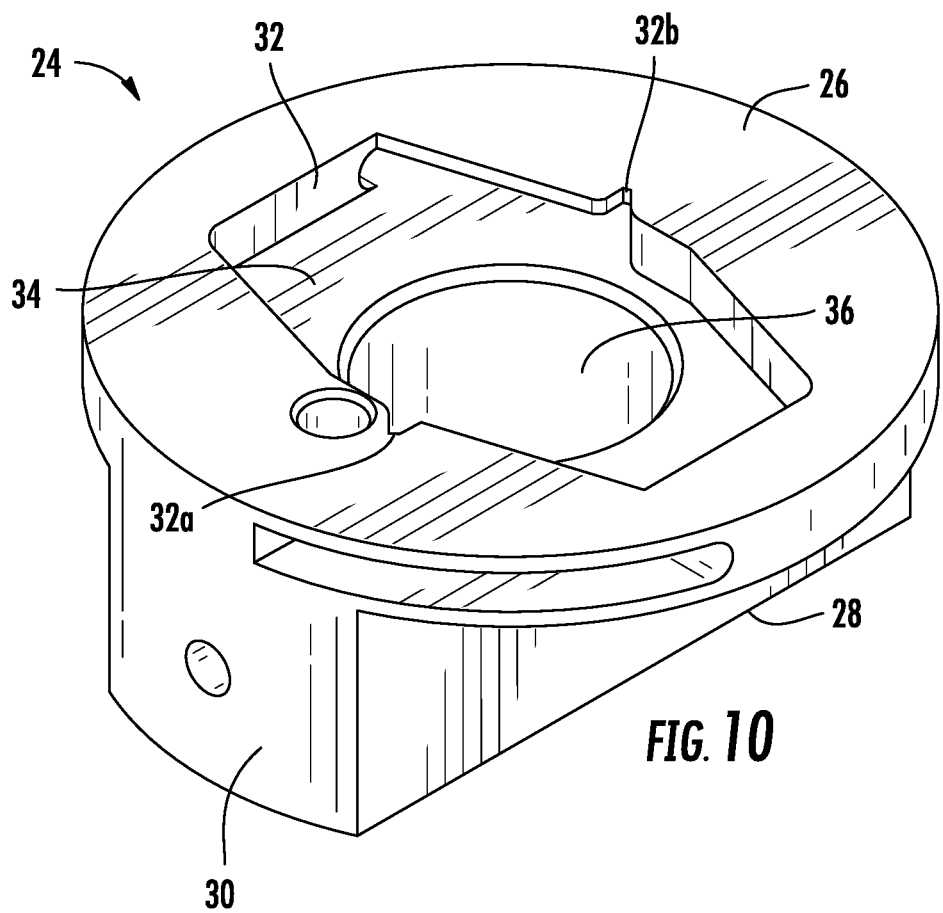
FIG. 10 is a perspective view of a syringe barrel holder of the syringe holder of FIG. 1, according to an exemplary embodiment.
Figure 11:
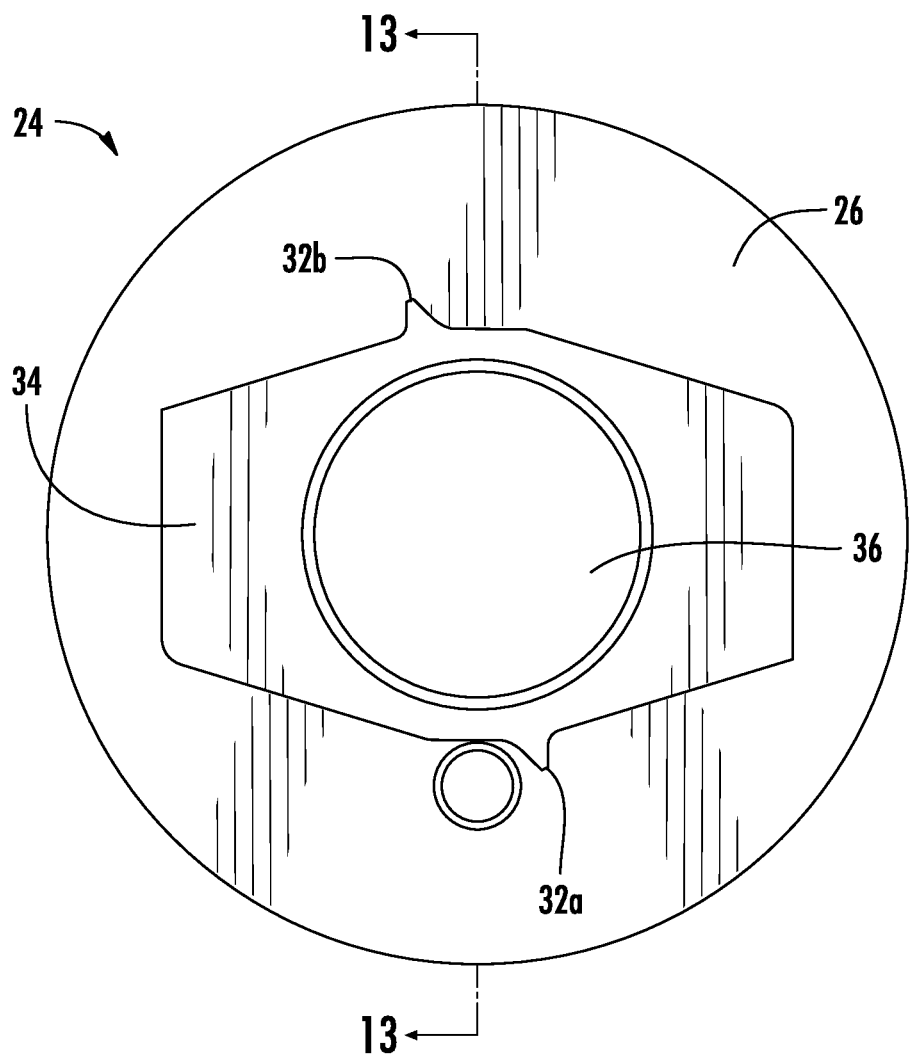
FIG. 11 is a top view of the syringe barrel holder of FIG. 10, according to an exemplary embodiment.
Figure 12:
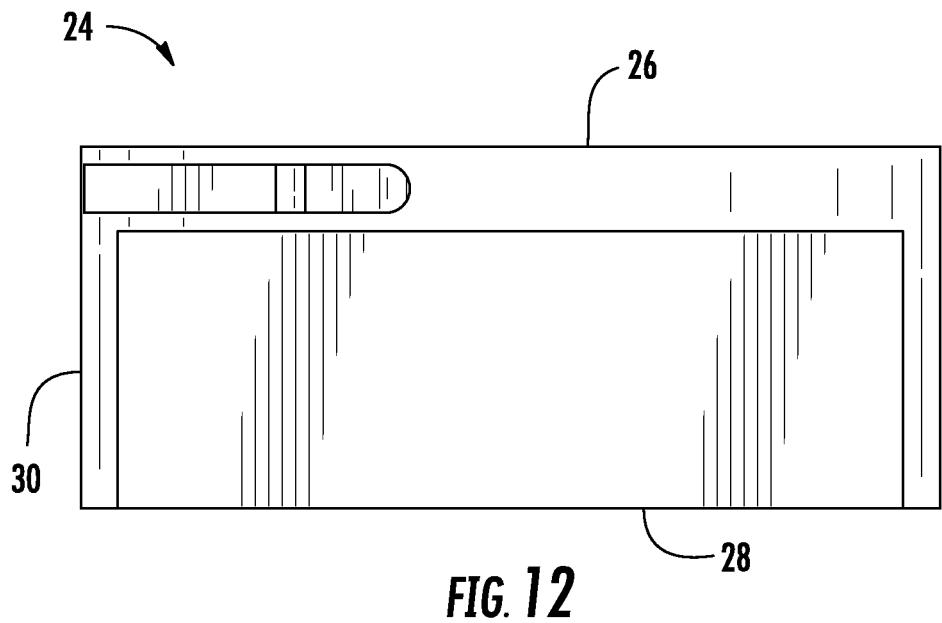
FIG. 12 is a side view of the syringe barrel holder of FIG. 10, according to an exemplary embodiment.
Figure 13:
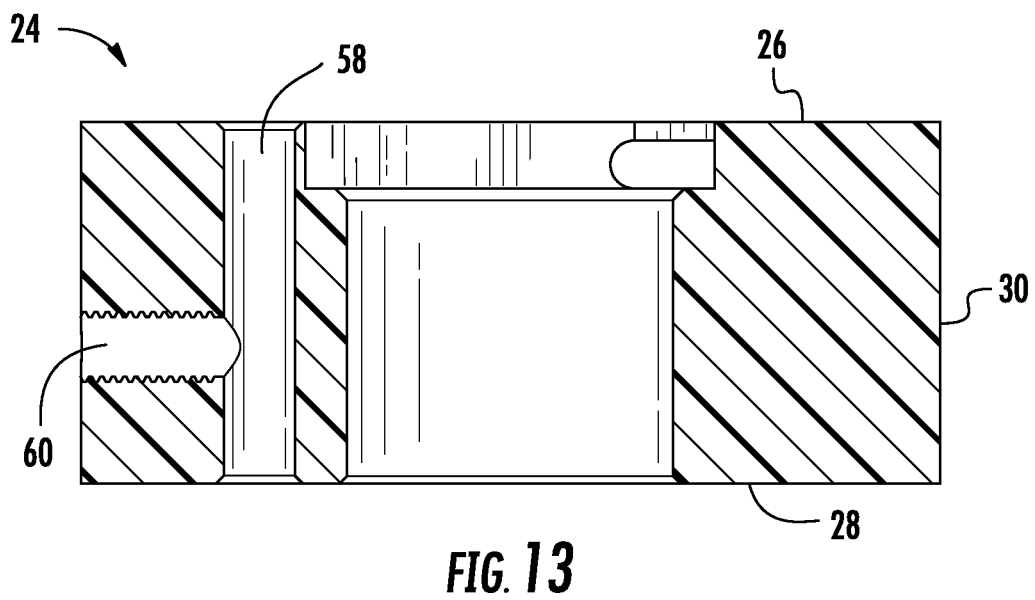
FIG. 13 is a sectional view of the syringe barrel holder taken along line 13-13 of FIG. 11, according to an exemplary embodiment.

Syringe holder 10 includes a syringe barrel holder 24 extending between a top surface 26 and a bottom surface 28 and bounded by an exterior surface 30 extending there-between, as detailed in FIGS. 10-12. Syringe barrel holder 24 has a depression 32 in top surface 26 (FIG. 10) which is configured to receive and engage finger tabs 14 of syringe 12 and has a bottom depression surface 34 (FIGS. 10 and 11) which is engageable by finger tabs 14. A barrel opening 36 receives barrel 12a of syringe 12. Barrel opening 36 includes a central longitudinal axis A-A (FIG. 2), a shaft channel 58 (FIG. 13) having a shaft axis B-B (FIG. 2) parallel to central longitudinal axis A-A, and a set screw channel 60 (FIG. 13) having a screw axis C-C (FIG. 2) passing through shaft channel 58.

Figure 14:
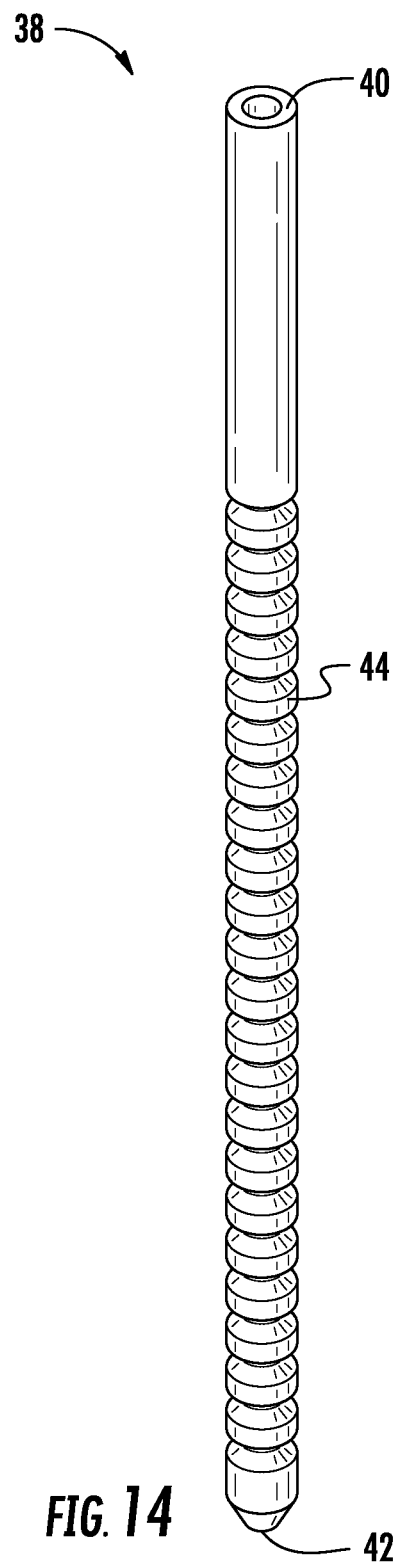
FIG. 14 is a perspective view of a dosing shaft of the syringe holder of FIG. 1, according to an exemplary embodiment.

As illustrated in FIGS. 1, 2 and 14, a dosing shaft 38 extends from a first end 40 to a second end 42 and includes a plurality of notches 44 between ends 40, 42. Notches 44 are equally spaced. Dosing shaft 38 is located and slideable within shaft channel 58.

Figure 3:
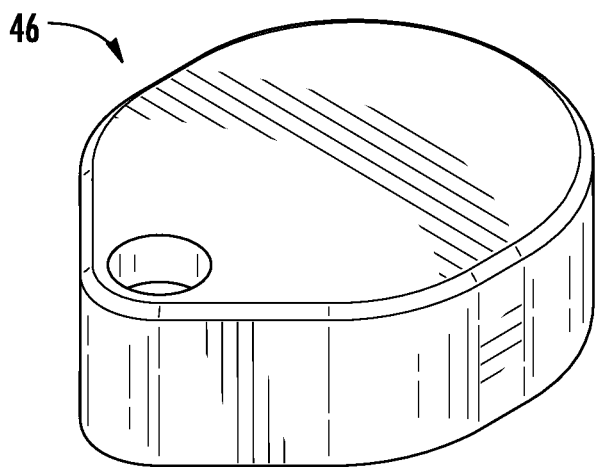
FIG. 3 is a perspective view of a plunger cap of the syringe holder of FIG. 1, according to an exemplary embodiment.
Figure 4:
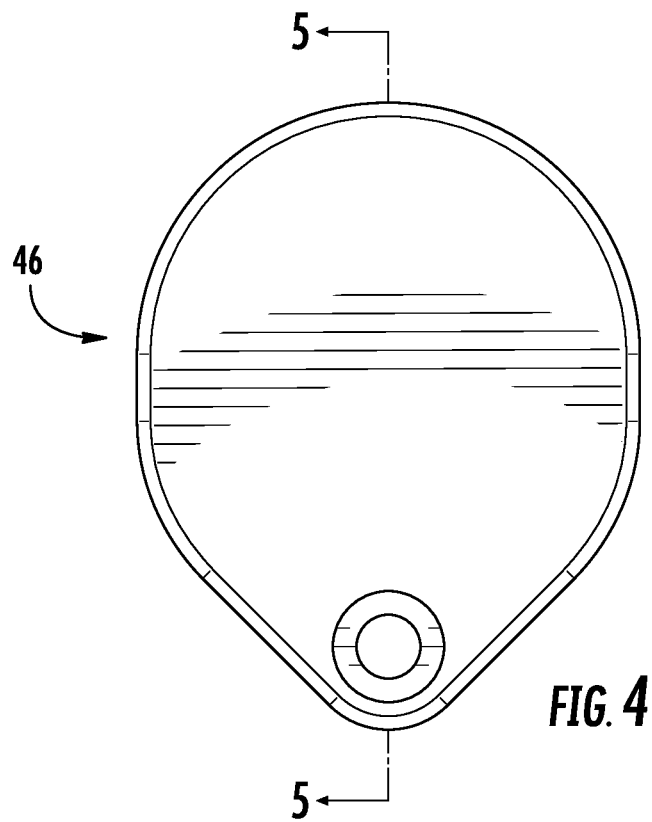
FIG. 4 is a top view of the plunger cap of FIG. 3, according to an exemplary embodiment.
Figure 5:
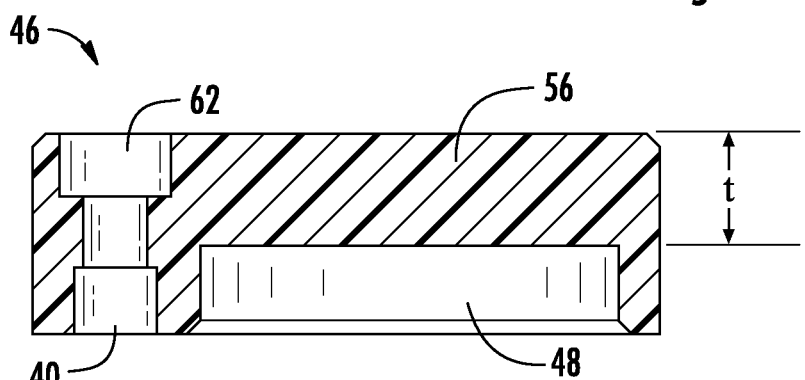
FIG. 5 is a sectional view of the plunger cap taken along line 5-5 of FIG. 4, according to an exemplary embodiment.

As detailed in FIGS. 3-5, a plunger cap 46 includes a plunger receptacle 48 and is attached to first end 40 of dosing shaft 38 such that plunger receptacle 48 receives finger pad 20 of plunger 12b when syringe 12 is positioned in barrel opening 36 (FIG. 2). By way of example, plunger cap 46 includes an opening into which first end 40 of dosing shaft 38 is located. First end 40 is threaded to receive a threaded fastener 62 (FIGS. 1, 2, 5) which retains plunger cap 46 in engagement with dosing shaft 38. Alternatively, and by way of example, plunger cap 46 could be welded to, adhered to, integrally formed with or friction-fit to dosing shaft 38.

Figure 6:
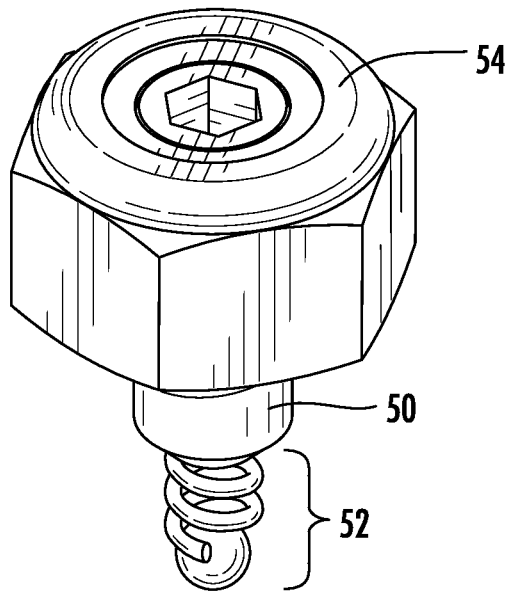
FIG. 6 is a perspective view of a socket set screw assembly of the syringe holder of FIG. 1, according to an exemplary embodiment.
Figure 7:
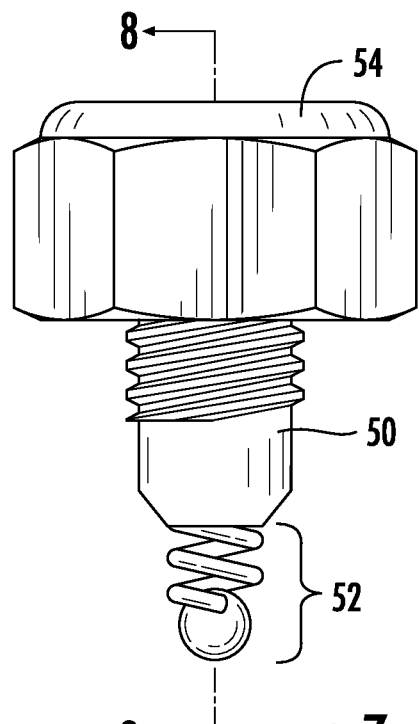
FIG. 7 is a side view of the socket set screw assembly of FIG. 6, according to an exemplary embodiment.
Figure 8:
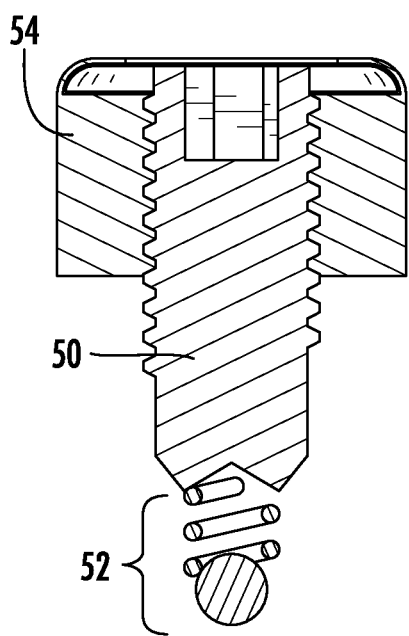
FIG. 8 is a sectional view of the socket set screw assembly taken along line 8-8 of FIG. 7, according to an exemplary embodiment.
Figure 9:
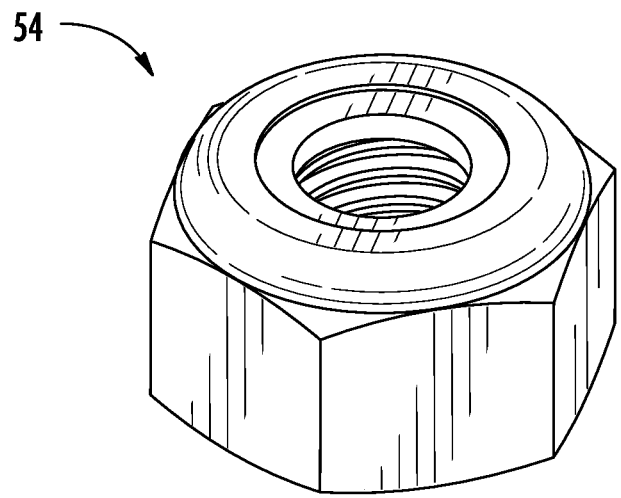
FIG. 9 is a perspective view of a locknut of the syringe holder of FIG. 1, according to an exemplary embodiment.

A socket set screw 50 (FIGS. 6-8) is located and engaged within set screw channel 60 (FIG. 13) and has a resilient end 52 engageable with notches 44 of dosing shaft 38 to permit discrete positioning of dosing shaft 38 within shaft channel 58.

In another embodiment of syringe holder 10, shaft axis B-B is on an angle relative to screw axis C-C. By providing a non-perpendicular orientation between shaft axis B-B and screw axis C-C, the force required to overcome the ratcheting of dosing shaft 38 relative to resilient end 52 can be made directional. In particular, if screw axis C-C is oriented such that socket set screw 50 is pointed somewhat downward (see FIG. 2), the force to move dosing shaft 38 downward should be lower than the force required to move dosing shaft 38 upward. The effect is to further inhibit movement of plunger 12b from within barrel 12a due to back pressure when applying an anesthetic drug. The angle of this downward orientation would be measured as a positive angle between shaft axis B-B and screw axis C-C.

In a specific embodiment, screw axis C-C is perpendicular to and intersects with shaft axis B-B.

As detailed in FIGS. 6-9, in a further embodiment of syringe holder 10, resilient end 52 of socket set screw 50 is a ball-and-spring, and a locknut 54 engages socket set screw 50 opposite the ball-and-spring.

In yet another embodiment of syringe holder 10, resilient end 52 of socket set screw 50 is a rubber grommet, and a locknut 54 engages socket set screw 50 opposite the rubber grommet.

As detailed in FIGS. 10 and 11, in yet a further embodiment of syringe holder 10, depression 32 of top surface 26 of syringe barrel holder 24 further comprises a first flange depression 32a opposite a second flange depression 32b to allow finger tabs 14 of barrel 12a to twist and lock into depression 32.

In yet another embodiment of syringe holder 10, plunger cap 46 (FIG. 5) has an internal wall 56 with a thickness, t, from 3.40 mm to 4.40 mm.

In yet a further embodiment of syringe holder 10, internal wall 56 (FIG. 5) has a thickness, t, from 3.65 mm to 4.15 mm. In a specific embodiment, internal wall 56 has a thickness, t, of 3.90 mm.

In yet another embodiment of syringe holder 10, notches 44 of dosing shaft 38 are spaced at increments of 3.0 mm to 4.0 mm.

In yet a further embodiment of syringe holder 10, notches 44 of dosing shaft 38 are spaced at increments of 3.5 mm.

It is contemplated that the presently preferred embodiment of the syringe holder would be fabricated from stainless steel. However, depending upon user and regulatory preference the holder may be fabricated from and alternative material such as plastic.

It should be understood that the figures illustrate the exemplary embodiments in detail, and it should be understood that the present application is not limited to the details or methodology set forth in the description or illustrated in the figures. It should also be understood that the terminology is for the purpose of description only and should not be regarded as limiting.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that any particular order be inferred. In addition, as used herein the article "a" is intended to include one or more than one component or element, and is not intended to be construed as meaning only one.

For purposes of this disclosure, the term "coupled" means the joining of two components directly or indirectly to one another. Such joining may be stationary in nature or movable in nature. Such joining may be achieved with the two members and any additional intermediate members being integrally formed as a single unitary body with one another, or with the two members and any additional member being attached to one another. Such joining may be permanent in nature or alternatively may be removable or releasable in nature. Various embodiments of the invention relate to any combination of any of the features, and any such combination of features may be claimed in this or future applications. Any of the features, elements, or components of any of the exemplary embodiments discussed above may be utilized alone or in combination with any of the features, elements, or components of any of the other embodiments discussed above.

In various exemplary embodiments, the relative dimensions, including angles, lengths and radii, as shown in the Figures are to scale. Actual measurements of the Figures will disclose relative dimensions, angles and proportions of the various exemplary embodiments. Various exemplary embodiments extend to various ranges around the absolute and relative dimensions, angles and proportions that may be determined from the Figures. Various exemplary embodiments include any combination of one or more relative dimensions or angles that may be determined from the Figures. Further, actual dimensions not expressly set out in this description can be determined by using the ratios of dimensions measured in the Figures in combination with the express dimensions set out in this description. In addition, in various embodiments, the present disclosure extends to a variety of ranges (e.g., plus or minus 30%, 20%, or 10%) around any of the absolute or relative dimensions disclosed herein or determinable from the Figures.

What is claimed is:

1. A syringe holder, for holding a syringe including a barrel and a plunger, the barrel defined by a length and an end pair of finger tabs, with a hole there-between, opposite an open end to dispense an anesthetic drug, the plunger defined by a length and a finger pad opposite a rubber seal, comprising:
    a syringe barrel holder extending between a top surface and a bottom surface and bounded by an exterior surface extending there-between, the syringe barrel holder having: a depression in the top surface configured to receive and engage the end pair of finger tabs of the syringe, the depression having a bottom depression surface which is engageable by the end pair of finger tabs, a barrel opening for receiving the barrel of the syringe, the barrel opening including a central longitudinal axis, a shaft channel having a shaft axis parallel to the central longitudinal axis, and a set screw channel having a screw axis passing through the shaft channel;
    a dosing shaft extending from a first end to a second end and including a plurality of notches between the first end and the second end, the plurality of notches being equally spaced, the dosing shaft being located and slideable within the shaft channel;
    a plunger cap including a plunger receptacle and attached to the first end of the dosing shaft such that the plunger receptacle receives the finger pad of the plunger when the syringe is positioned in the barrel opening; and
    a socket set screw located and engaged within the set screw channel and having a resilient end engageable with the plurality of notches of the dosing shaft to permit discrete positioning of the dosing shaft within the shaft channel.

2. The syringe holder of claim 1, wherein the screw axis is perpendicular to and intersects with the shaft axis.

3. The syringe holder of claim 1, wherein the resilient end of the socket set screw is a ball-and-spring, and a locknut engages the socket set screw opposite the ball-and-spring.

4. The syringe holder of claim 1, wherein the resilient end of the socket set screw is a rubber grommet, and a locknut engages the socket set screw opposite the rubber grommet.

5. The syringe holder of claim 1, wherein the depression of the top surface of the syringe barrel holder further comprises a first flange depression opposite a second flange depression to allow the end pair of finger tabs of the barrel to twist and lock into the depression.

6. The syringe holder of claim 1, wherein the plunger cap has an internal wall with a thickness from 3.40 mm to 4.40 mm.

7. The syringe holder of claim 6, wherein the internal wall has the thickness from 3.65 mm to 4.15 mm.

8. The syringe holder of claim 1, wherein the plurality of notches of the dosing shaft are spaced at increments of 3.0 mm to 4.0 mm.

9. The syringe holder of claim 8, wherein the plurality of notches of the dosing shaft are spaced at increments of 3.5 mm.

10. A syringe holder, for holding a syringe including a barrel and a plunger, the barrel defined by a length and an end pair of finger tabs, with a hole there-between, opposite an open end to dispense an anesthetic drug, the plunger defined by a length and a finger pad opposite a rubber seal, comprising:
    a syringe barrel holder extending between a top surface and a bottom surface and bounded by an exterior surface extending there-between, the syringe barrel holder having: a depression in the top surface configured to receive and engage the end pair of finger tabs of the syringe, the depression having a bottom depression surface which is engageable by the end pair of finger tabs, a barrel opening for receiving the barrel of the syringe, the barrel opening including a central longitudinal axis, a shaft channel having a shaft axis parallel to the central longitudinal axis, and a set screw channel having a screw axis passing through the shaft channel, the screw axis perpendicular to and intersecting with the shaft axis;

a dosing shaft extending from a first end to a second end and including a plurality of notches between the first end and the second end, the plurality of notches being equally spaced at increments of 3.0 mm to 4.0 mm, the dosing shaft being located and slideable within the shaft channel;

a plunger cap including a plunger receptacle and attached to the first end of the dosing shaft such that the plunger receptacle receives the finger pad of the plunger when the syringe is positioned in the barrel opening, the plunger cap having an internal wall with a thickness from 3.40 mm to 4.40 mm; and a socket set screw located and engaged within the set screw channel and having a resilient end engageable with the plurality of notches of the dosing shaft to permit discrete positioning of the dosing shaft within the shaft channel.

11. The syringe holder of claim 10, wherein the resilient end of the socket set screw is a ball-and-spring, and a locknut engages the socket set screw opposite the ball-and-spring.

12. The syringe holder of claim 10, wherein the resilient end of the socket set screw is a rubber grommet, and a locknut engages the socket set screw opposite the rubber grommet.

13. The syringe holder of claim 10, wherein the depression of the top surface of the syringe barrel holder further comprises a first flange depression opposite a second flange depression to allow the end pair of finger tabs of the barrel to twist and lock into the depression.

14. The syringe holder of claim 10, wherein the internal wall has the thickness from 3.65 mm to 4.15 mm.

15. The syringe holder of claim 10, wherein the plurality of notches of the dosing shaft are spaced at increments of 3.5 mm.

16. A syringe holder, for holding a syringe including a barrel and a plunger, the barrel defined by a length and an end pair of finger tabs, with a hole there-between, opposite an open end to dispense an anesthetic drug, the plunger defined by a length and a finger pad opposite a rubber seal, comprising:

a syringe barrel holder extending between a top surface and a bottom surface and bounded by an exterior surface extending there-between, the syringe barrel holder having: a depression in the top surface configured to receive and engage the end pair of finger tabs of the syringe, the depression having a bottom depression surface which is engageable by the end pair of finger tabs and a first flange depression opposite a second flange depression to allow the end pair of finger tabs of the barrel to twist and lock into the depression, a barrel opening for receiving the barrel of the syringe, the barrel opening including a central longitudinal axis, a shaft channel having a shaft axis parallel to the central longitudinal axis, and a set screw channel having a screw axis passing through the shaft channel, the screw axis perpendicular to and intersecting with the shaft axis;

a dosing shaft extending from a first end to a second end and including a plurality of notches between the first end and the second end, the plurality of notches being equally spaced at increments of 3.0 mm to 4.0 mm, the dosing shaft being located and slideable within the shaft channel;

a plunger cap including a plunger receptacle and attached to the first end of the dosing shaft such that the plunger receptacle receives the finger pad of the plunger when the syringe is positioned in the barrel opening, the plunger cap having an internal wall with a thickness from 3.40 mm to 4.40 mm; and a socket set screw located and engaged within the set screw channel and having a resilient end engageable with the plurality of notches of the dosing shaft to permit discrete positioning of the dosing shaft within the shaft channel.

17. The syringe holder of claim 16, wherein the resilient end of the socket set screw is a ball-and-spring, and a locknut engages the socket set screw opposite the ball-and-spring.

18. The syringe holder of claim 16, wherein the resilient end of the socket set screw is a rubber grommet, and a locknut engages the socket set screw opposite the rubber grommet.

19. The syringe holder of claim 16, wherein the internal wall has the thickness from 3.65 mm to 4.15 mm.

20. The syringe holder of claim 16, wherein the plurality of notches of the dosing shaft are spaced at increments of 3.5 mm.

* * * * *